US006395723B2

(12) United States Patent
Kagan et al.

(10) Patent No.: US 6,395,723 B2
(45) Date of Patent: May 28, 2002

(54) METHOD OF PROVIDING COGINITION ENHANCEMENT WITH 5α-PREGNAN-3β-OL-20-ONE SULFATE

(75) Inventors: Michael Z. Kagan, Plainsboro; Syed M. Shah, East Hanover, both of NJ (US)

(73) Assignee: Wyeth, Madison, NJ (US)

( * ) Notice: Subject to any disclaimer, the term of this patent is extended or adjusted under 35 U.S.C. 154(b) by 0 days.

(21) Appl. No.: 09/971,159

(22) Filed: Oct. 4, 2001

Related U.S. Application Data

(62) Division of application No. 09/396,049, filed on Sep. 15, 1999, now abandoned, which is a continuation of application No. 09/064,994, filed on Apr. 23, 1998, now abandoned.
(60) Provisional application No. 60/045,359, filed on May 2, 1997.

(51) Int. Cl.$^7$ .............................. A61K 3/57; C07J 5/00; C07J 31/00
(52) U.S. Cl. ........................ 514/182; 552/557; 552/609
(58) Field of Search ......................... 514/182; 552/557, 552/609

(56) References Cited

U.S. PATENT DOCUMENTS

| 2,834,712 | A |   | 5/1958 | Beall et al. |
| 3,608,077 | A |   | 9/1971 | Ginsig |
| 4,154,820 | A |   | 5/1979 | Simoons |
| 4,663,311 | A |   | 5/1987 | Tenu et al. |
| 5,292,730 | A |   | 3/1994 | Lardy |
| 6,083,941 | A | * | 7/2000 | Farb ........................... 514/177 |

FOREIGN PATENT DOCUMENTS

| WO | WO 93/03732 | 3/1993 |
| WO | WO 95/21617 | 8/1995 |
| WO | WO 96/16076 | 5/1996 |

OTHER PUBLICATIONS

Park–Chung et al., Distinct Sites for Inverse Modulation of N–Methyl–D–Aspartate Receptors by Sulfated Steroids, Molecular Pharmacology, 52:1113–1123, Dec. 1997.
Axelson, M., Endocrinology, 1984, 114(2), pp. 337–344.
Baillie, T.A. et al., J. Ster. Biochem. 1980, 13, pp. 1473–1488.
Borodinsky, L.N. et al., Neurochem Int., 1997, 31(2), pp. 313–317.
Brot, M.D. et al., Eur. J. Pharmaco, 1997, 325, pp. 1–7.
de Wit, H., et al., Psychopharmoc, 1997, 130, pp. 69–78.
Friess, E., et al., Amer. J. Physiol., 1997, 272(5,Pt.1), pp. E885–E891.
Irwin, R.P. et al., J. Pharmacol. and Exp. Thera., 1994, 271(2), pp. 677–682.
Labella, F., et al., Dev. Neurosci., 1978, 4(Charact & Funct. Opiods), pp. 361–362.
Le Foll, F., et al., Eur. J. Pharmacol, 1997, 331, pp. 303–311.
Mickan, H. et al., J. Ster. Biochem, 1979, 11, pp. 1455–1459.
Mickan, H., et al., J. Ster. Biochem., 1979, 11, pp. 1461–1466.
Mickan, H. et al., J. Ster. Biochem., 1979, 11, pp. 1467–1470.
Murray, H.E., et al., J. Neuroendocr, 1997, 9, pp. 287–295.
Poisbeau, P. et al., J. Physiol. 1997, 500.2, pp. 475–485.
Ravasio, N., et al., J. Org. Chem., 1993, 58, pp. 1259–1261.
Reddy, D.S. et al., Brain Res., 1997, 752, pp. 61–71.
Sahlberg, B.L., et al., J. Ster. Biochem., 1986, 25 (3) 379–391.
Schultz, A.G., et al., J. Org. Chem., 1996, pp. 4857–4859.
Simada, K., et al., J. Liq. Chromato, 1995, 18(9), pp. 1691–1701.
Simada, K., et al., Anal. Sci., 1995, 11, pp. 445–447.
Van Eldere, J.R. et al., Appl. Environ. Microbiol., 1987, 53(7), 1655–1660.
Vanluchene, E., et al., J. Ster. Biochem., 1984, 21(4), pp. 367–371.
Vanover, K.E., Eur. J. Pharmacol., 1997, 327, pp. 97–101.
Vivian, J.A., et al., J. Pharmacol..and Exp. Thera., 1997, 282(1), pp. 318–325.
Wang, M.D. et al., Acta Physiol Scand. 1997, 159, pp. 343–344.
Park–Chung M., et al. Mol. Pharmacol., 46(1), Jul. 1994, pp. 146–150.
Townsley J.D., Endocrinology, 93, 1972, pp. 172–181.
Bitran, D., et al., Brain Res. 561(1), Oct. 4, 1991, pp. 157–161.
El–etr., M. et al., Brain Res., 790, 1998, pp. 334–338.
Flood et al., Proc. Natl. Acad. Sci., vol. 89, pp. 1567–1571, 1992.

* cited by examiner

*Primary Examiner*—John S. Brusca
*Assistant Examiner*—Marjorie A. Moran
(74) *Attorney, Agent, or Firm*—Arnold S. Milowsky

(57) ABSTRACT

This invention provides a method of providing progestational therapy to a mammal in need thereof which comprises administering a progestationally effective amount of a pharmaceutically acceptable salt of 5α-pregnan-3β-ol-20-one 3-sulfate ester to said mammal.

2 Claims, No Drawings

METHOD OF PROVIDING COGINITION ENHANCEMENT WITH 5α-PREGNAN-3β-OL-20-ONE SULFATE

This application divisional of U.S. application Ser. No. 09/396,049, filed Sep. 15, 1999, now abandoned, which is a continuation of U.S. application Ser. No. 09/064,994, filed Apr. 23, 1998, now abandoned, which claims priority of U.S. Provisional Application No. 60/045,359, filed May 2, 1997.

BACKGROUND OF THE INVENTION

The use of naturally occurring estrogenic compositions of substantial purity and low toxicity such as PREMARIN (conjugated equine estrogens) has become a preferred medical treatment for alleviating the symptoms of menopausal syndrome, osteoporosis/osteopenia in estrogen deficient women and in other hormone related disorders. The estrogenic components of the naturally occurring estrogenic compositions have been generally identified as sulfate esters of estrone, equilin, equilenin, 17-β-estradiol, dihydroequilenin and 17-β-dihydroequilenin (U.S. Pat. No. 2,834,712). The estrogenic compositions are usually buffered or stabilized with alkali metal salts of organic or inorganic acids at a substantially neutral pH of about 6.5 to 7.5. Urea has also been used as a stabilizer (U.S. Pat. No. 3,608,077). The incorporation of antioxidants to stabilize synthetic conjugated estrogens and the failure of pH control with tris (hydroxymethyl)aminomethane (TRIS) to prevent hydrolysis is discussed in U.S. Pat. No. 4,154,820.

One of the compounds described herein, 5α-pregnan-3β-ol-20-one 3-sulfate ester sodium salt is a minor component of PREMARIN (conjugated equine estrogens), and is also commercially available.

DESCRIPTION OF THE INVENTION

In accordance with this invention, there is providing progestational therapy to a mammal in need thereof, which comprises administering a pharmaceutically acceptable salt of 5α-pregnan-3β-ol-20-one 3-sulfate ester to said mammal. This invention also provides a method of providing progestational therapy to a mammal in need thereof, which comprises administering a composition of matter consisting essentially of a pharmaceutically acceptable salt of 5α-pregnan-3β-ol-20-one 3-sulfate ester to said mammal.

Pharmaceutically acceptable salts of 5α-pregnan-3β-ol-20-one 3-sulfate ester include, but are not limited to, the alkali metal salts, alkaline earth metal salts, ammonium salts, alkylammonium salts containing 1–6 carbon atoms or dialkylammonium salts containing 1–6 carbon atoms in each alkyl group, and trialkylammonium salts containing 1–6 carbon atoms in each alkyl group.

The compounds of this invention can be prepared from readily available starting materials using standard literature techniques or can be purchased, as with 5α-pregnan-3β-ol-20-one 3-sulfate ester sodium salt.

The progestational activity of a representative compound of this invention (5α-pregnan-3β-ol-20-one 3-sulfate ester sodium salt) was evaluated in an in vitro standard pharmacological test procedure. The procedure used and results obtained are briefly described below.

The results of these standard pharmacological test procedures demonstrate that the compounds of this invention are progestational. In this test procedure, the progestational activity of a compound is quantified based on its stimulation of alkaline phosphatase enzyme activity in T47D cells, a human breast cancer cell line which expresses high levels of progesterone receptors. This is a well established test procedure in which both the progestin receptors and the response stimulated by activated progestin receptors are endogenous to the cells. Cells are pre-conditioned in low serum medium for one day and then treated with test compounds. Alkaline phosphatase activity is measured 24 hr after treatment Reference progestins, such as progesterone and medroxyprogesterone acetate, induce a 30–60 fold induction of alkaline phosphatase requiring only low nanomolar concentrations for activity. The alkaline phosphatase activity induced by progestins is blocked or inhibited by progestin receptor antagonists such as RU486 indicating the specificity of the response. When evaluated in this test procedure, 5α-pregnan-3β-ol-20-one 3-sulfate ester sodium salt, had an $IC_{50}$ of $5 \times 10^{-6}$ demonstrating progestational activity.

The neuroprotective and cognition enhancing effects of the compounds of this invention were evaluated in an in vitro standard pharmacological test procedure which measured the effects of 5α-pregnan-3β-ol-20-one 3-sulfate ester sodium salt, as a representative compound of this invention, on calcium and potassium channel currents. Briefly, the following procedure was used.

Whole cell recording techniques were used to record calcium and potassium currents from cultured hippocampal neurons. The compounds to be evaluated were made fresh each day in a 400 $\mu$M ethanol stock solution. The test compounds were diluted in saline to obtain a final concentration of 2 $\mu$M. The amplitude of calcium or potassium currents in control, test compound, and washout solutions was measured from at least 10 current traces for each condition. To compensate for rundown of the calcium current with time, control and washout currents were averaged. The current amplitude with drug was divided by the averaged control and washout current to determine the percent change. The means, standard deviations and errors for each test compound were calculated and significance from control was determined using the paired T-Test. 5α-Pregnan-3β,20β-diol enhanced increased potassium channel currents versus control by 21.76±2.40% (p=0.0006), indicating that 5α-pregnan-3β,20β-diol hyperpolarizes neurons, thereby allowing them to respond more readily to other stimuli. Calcium channel currents were significantly decreased (p=0.044) from control decrease by 4.64±1.64% versus control) demonstrating the neuroprotective effects of 5α-pregnan-3β-ol-20-one 3-sulfate ester sodium salt,. These results show that the compounds of this invention are useful as neuroprotective agents, in protecting against epileptic seizures, and in cognition enhancement.

The compounds of this invention are progestational agents. Based on the results obtained in the standard pharmacological test procedures, the compounds of the invention are useful as oral contraceptives (male and female), in hormone replacement therapy (particularly when combined with an estrogen), in the treatment of endometriosis luteal phase defects, benign breast and prostatic diseases and prostatic and endometrial cancers. The compounds of this invention are also useful in protecting against epileptic seizures, in cognition enhancement, in treating Alzheimer's disease, dementias, vasomotor symtpoms related to menopause, and other central nervous system disorders. The compounds of this invention are further useful in stimulating erythropoises.

The compounds of this invention can be used alone as a sole therapeutic agent or can be used in combination with other agents, such as other estrogens, progestins, or and androgens.

The compounds of this invention can be formulated neat or with a pharmaceutical carrier for administration, the proportion of which is determined by the solubility and chemical nature of the compound, chosen route of administration and standard pharmacological practice. The pharmaceutical carrier may be solid or liquid.

A solid carrier can include one or more substances which may also act as flavoring agents, lubricants, solubilizers, suspending agents, fillers, glidants, compression aids, binders or tablet-disintegrating agents; it can also be an encapsulating material. In powders, the carrier is a finely divided solid which is in admixture with the finely divided active ingredient. In tablets, the active ingredient is mixed with a carrier having the necessary compression properties in suitable proportions and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Liquid carriers are used in preparing solutions, suspensions, emulsions, syrups, elixirs and pressurized compositions. The active ingredient can be dissolved or suspended in a pharmaceutically acceptable liquid carrier such as water, an organic solvent, a mixture of both or pharmaceutically acceptable oils or fats. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (partially containing additives as above, e.g. cellulose derivatives, preferably sodium carboxymethyl cellulose solution), alcohols (including monohydric alcohols and polyhydric alcohols, e.g. glycols) and their derivatives, lethicins, and oils (e.g. fractionated coconut oil and arachis oil). For parenteral administration, the carrier can also be an oily ester such as ethyl oleate and isopropyl myristate. Sterile liquid carriers are useful in sterile liquid form compositions for parenteral administration. The liquid carrier for pressurized compositions can be halogenated hydrocarbon or other pharmaceutically acceptable propellant.

Liquid pharmaceutical compositions which are sterile solutions or suspensions can be utilized by, for example, intramuscular, intraperitoneal or subcutaneous injection. Sterile solutions can also be administered intravenously. The compounds of this invention can also be administered orally either in liquid or solid composition form.

The compounds of this invention may be administered rectally or vaginally in the form of a conventional suppository. For administration by intranasal or intrabronchial inhalation or insufflation, the compounds of this invention may be formulated into an aqueous or partially aqueous solution, which can then be utilized in the form of an aerosol. The compounds of this invention may also be administered transdermally through the use of a transdermal patch containing the active compound and a carrier that is inert to the active compound, is non toxic to the skin, and allows delivery of the agent for systemic absorption into the blood stream via the skin. The carrier may take any number of forms such as creams and ointments, pastes, gels, and occlusive devices. The creams and ointments may be viscous liquid or semisolid emulsions of either the oil-in-water or water-in-oil type. Pastes comprised of absorptive powders dispersed in petroleum or hydrophilic petroleum containing the active ingredient may also be suitable. A variety of occlusive devices may be used to release the active ingredient into the blood stream such as a semipermiable membrane covering a reservoir containing the active ingredient with or without a carrier, or a matrix containing the active ingredient. Other occlusive devices are known in the literature.

The dosage requirements vary with the particular compositions employed, the route of administration, the severity of the symptoms presented and the particular subject being treated. Based on the results obtained in the standard pharmacological test procedures, projected daily dosages of active compound would be 0.02 $\mu$g/kg–750 $\mu$g/kg. Treatment will generally be initiated with small dosages less than the optimum dose of the compound. Thereafter the dosage is increased until the optimum effect under the circumstances is reached; precise dosages for oral, parenteral, nasal, or intrabronchial administration will be determined by the administering physician based on experience with the individual subject treated. Preferably, the pharmaceutical composition is in unit dosage form, e.g. as tablets or capsules. In such form, the composition is sub-divided in unit dose containing appropriate quantities of the active ingredient; the unit dosage forms can be packaged compositions, for example, packeted powders, vials, ampoules, prefilled syringes or sachets containing liquids. The unit dosage form can be, for example, a capsule or tablet itself, or it can be the appropriate number of any such compositions in package form.

What is claimed is:

1. A method of providing cognition enhancement to a mammal in need thereof which comprises administering a cognition enhancement effective amount of a pharmaceutically acceptable salt of 5$\alpha$-pregnan-3$\beta$-ol-20-one 3-sulfate ester to said mammal.

2. The method according to claim 1, wherein the pharmaceutically acceptable salt of the 3-sulfate ester is an alkali metal salt, alkaline earth metal salt, ammonium salt, alkylammonium salt containing 1–6 carbon atoms, or dialkylammonium salt containing 1–6 carbon atoms in each alkyl group, or trialkylammonium salt containing 1–6 carbon atoms in each alkyl group.

* * * * *